US008623651B2

(12) United States Patent
Sun et al.

(10) Patent No.: US 8,623,651 B2
(45) Date of Patent: Jan. 7, 2014

(54) **ENHANCIN GENE BEL1 FROM *BACILLUS THURINGIENSIS* AND ITS USE IN BIOLOGICAL INSECTICIDE**

(75) Inventors: Ming Sun, Wuhan (CN); Ziniu Yu, Wuhan (CN); Shangling Fang, Wuhan (CN); Donghai Peng, Wuhan (CN); Lifang Ruan, Wuhan (CN); Shouwen Chen, Wuhan (CN); Chunping Luo, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 93 days.

(21) Appl. No.: 13/133,429

(22) PCT Filed: Nov. 23, 2009

(86) PCT No.: PCT/CN2009/001303
§ 371 (c)(1),
(2), (4) Date: Aug. 22, 2011

(87) PCT Pub. No.: WO2010/066092
PCT Pub. Date: Jun. 17, 2010

(65) Prior Publication Data
US 2012/0156167 A1    Jun. 21, 2012

(30) Foreign Application Priority Data

Dec. 9, 2008  (CN) .......................... 2008 1 0236718

(51) Int. Cl.
*C12N 15/32*  (2006.01)
*C12N 15/82*  (2006.01)
*C12N 1/00*  (2006.01)
*C07K 14/325*  (2006.01)

(52) U.S. Cl.
USPC ........ 435/419; 435/468; 536/23.71; 530/350; 424/93.2

(58) Field of Classification Search
USPC ................ 435/419, 468; 536/23.71; 530/350; 424/93.2
See application file for complete search history.

(56) References Cited

U.S. PATENT DOCUMENTS 5,475,090 A    12/1995   Granados et al.

FOREIGN PATENT DOCUMENTS

CN         1401772 A      3/2003

OTHER PUBLICATIONS

C3EN91_BACTK ; C3EN91; Jun. 16, 2009, integrated into UniProtKB/TrEMBL. Jun. 16, 2009, sequence version 1. SCORE search Result No. 2.*

Zwick et al., Genome Res. Aug. 2012;22(8):1512-24. doi: 10.1101/gr.134437.111. Epub May 29, 2012. Genomic characterization of the *Bacillus cereus* sensu lato species: backdrop to the evolution of *Bacillus anthracis*.*
Genome sequence of *Bacillus cereus* AH1134. RL Submitted (Sep. 2008) to the EMBL/GenBank/DDBJ databases. See Result 7 of Score Search result forApplication 13133429.*
Arantes, O., et al., "Construction of cloning vectors for *Bacillus thuringiensis*," Gene, 1991, vol. 108, pp. 115-119.
Bradford, M.M., "A Rapid and Sensitive Method for the Quantitation of Microgram Quantities of Protein Utilizing the Principle of Protein-Dye Binding," Analytical Biochemistry, 1976, vol. 72, pp. 248-254.
Fang, S., et al., "*Bacillus thuringiensis* Bel Protein Enhances the Toxicity of Cry1Ac Protein to *Helicoverpa armigera* Larvae by Degrading Insect Intestinal Mucin," Applied and Environmental Microbiology, Aug. 2009, pp. 5237-5243.
Hajaij-Ellouze, M., et al., "The enhancin-like metalloprotease from the *Bacillus cereus* group is regulated by the pleiotropic transcriptional activator PlcR but is not essential for larvicidal activity," FEMS Microbiol Lett, 2006, vol. 260, pp. 9-16.
Hilder, V.A., et al., "A novel mechansim of insect resistance engineered into tobacco," Nature, Nov. 12, 1987, vol. 300, pp. 160-163.
Laemmli, U.K., "Cleavage of Structural Proteins during the Assembly of the Head of Bacteriophage T4," Nature, Aug. 15, 1970, vol. 227, pp. 680-685.
Pardo-López, L., et al., "Strategies to improve the insecticidal activity of Cry toxins from *Bacillus thuringiensis*," Peptides, 2008, doi:10. 1016/j. peptides.2008.07.027.
Regev, A., et al., "Synergistic Activity of a *Bacillus thuringiensis* δ-Endotoxin and a Bacterial Endochitinase against *Spodoptera littoralis* Larvae," Applied and Environmental Microbiology, Oct. 1996, vol. 62, No. 10, pp. 3581-3586.
Schnepf, E., et al., "*Bacillus thuringiensis* and Its Pesticidal Crystal Proteins," Microbiology and Molecular Biology Reviews, Sep. 1998, pp. 775-806.
Sun, M., et al., "Characterization of the insecticidal crystal protein genes of *Bacillus thuringensis* YBT-1520," Acta Microbiologica Sinica, Aug. 2000, vol. 40, No. 4, pp. 365-371.
Li, L., et al., "Screening of acrystalliferous mutants from *Bacillus thuringiensis* and their transformation properties," Acta Microbiologica Sinica, Feb. 2000, vol. 40, No. 1, pp. 395-399.
Shen Juqun et al., Bioassay Procedures and Methods of Standardization of *Bacillus thuringiensis*, 1990, Chinese Journal of Biological Control, 1990, pp. 12-16.

(Continued)

*Primary Examiner* — Maria Leavitt
(74) *Attorney, Agent, or Firm* — Novak Druce Connolly Bove + Quigg LLP (57) ABSTRACT

The isolation, cloning of an enhancin gene bel1 from *Bacillus thuringiensis*, and the use of an enhancin Bel1 in biological insecticides are disclosed in the present invention. A new enhancin gene bel1 is isolated from *Bacillus thuringiensis* subsp. *kurstaki* YBT-1520, and its encoded product is a new enhancin Bel1. The enhancin has very strong effect-enhancing activity on the insecticidal action of insecticidal crystal protein Cry1Ac in killing Lepidoptera insects. The insecticidal activity of genetically engineered *Bacillus thuringiensis* BMB0187 developed on the basis of this enhancin is 5.7 times as high as that of the initial strain.

5 Claims, 9 Drawing Sheets

(56) References Cited

OTHER PUBLICATIONS

Wu Lan et al., A New Resolution Vector with cry1Ac10 Gene Based on *Bacillus thuringiensis* Transposon Tn4430, Acta Microbiol Sinica, Jun. 2000, vol. 40, No. 3, pp. 264-269.

*Bacillus thuringiensis* metalloprotease enhancin (mpbe) gene, promoter region and complete cds., Database Accession No. DQ151839, Nov. 1, 2005.
*Bacillus thuringiensis* serovar kurstaki, Database Accession No. FJ644934, Feb. 24, 2009.

* cited by examiner

ENHANCIN GENE BEL1 FROM *BACILLUS THURINGIENSIS* AND ITS USE IN BIOLOGICAL INSECTICIDE

TECHNICAL FIELD

The present invention pertains to the field of applied technologies of microorganisms. In particular, the present invention relates to the isolation, cloning of an enhancin gene from *Bacillus thuringiensis*, and the use of the protein encoded thereby in biological insecticides, which is associated with genetic engineering and microorganism agricultural chemicals.

BACKGROUND ART

*Bacillus thuringiensis*, Bt, is a Gram-positive rod-shaped bacterium widely existing in various ecological environments. The most notable characteristic of the species is to form hypopus of endogenous spore during the growth cycle thereof whilst generating parasporal crystal consisting of insecticidal crystal proteins (ICPs) having specific toxicity towards a wide variety of insects. These insecticidal crystal proteins have specific bioactivity on over 500 types of insects of 10 orders of insecta such as Lepidoptera, Diptera, Coleoptera, Hymenoptera, Homoptera, etc. and some pests in Protozoa, Nemathelminthes, Platyhelminthes and so on (Schnepf H E, Crickmore N, Rie J V, Lereclus D, Baum J, Feitelson J, Zeigler D R, Dean D H. 1998. *Bacillus thuringiensis* and its pesticidal crystal proteins. *Microbiol Mol Biol Rev*, 62: 775-806). *Bacillus thuringiensis* is widely applied to the development of biological insecticides as it has high insecticidal activity on various types of insects and the advantages of no harm to environment and human and livestock and so on. The biological insecticides developed on the basis of *Bacillus thuringiensis* has been the most successful biological agricultural chemical up to now, occupying more than 90% market of the whole industry of biological agricultural chemical and widely used for the control of pests in agriculture, forestry and storage industry. At the same time, people continue transferring genes of insecticidal crystal proteins of *Bacillus thuringiensis* into plants so as to construct transgenic plants for the control of agricultural pests.

*Bacillus thuringiensis* insecticides initially were produced by using the screened wide-type strains. Despite many advantages of *Bacillus thuringiensis*, the field applications thereof still lead to the problems of unstable control effects, short residual period, slow rate of killing pests and insensitivity to some target pests and so on. As molecular biology is flourishing, people start to genetically modify wide-type strains by means of genetic engineering to improve the insecticidal activities of the initial strains and prolong the residual periods thereof. However, while the applications of *Bacillus thuringiensis* insecticides are continuously spread and the application intensities are increasing, scientists continuously find the phenomena of the chemical resistance of target pests. These factors seriously limit the applications and popularization of insecticide products of *Bacillus thuringiensis* and are a menace to the rapid development of the whole industry. One effective solution to the problem is to find new insecticidal effect-enhancing factors for remarkably improving the insecticidal activities of the initial strains and postponing or overcoming the resistance of insects thereon.

Recently, searches for new insecticidal effect-enhancing factors have been the most prosperous part in the field of the applications and researches of *Bacillus thuringiensis*. Hilder et al. increased the insecticidal activities of the insecticidal crystal proteins generated by *Bacillus thuringiensis* by over 20 times by using serine protease inhibitors (Hilder V A, Gatehouse A M R, Sheerman S E, Barrer R F, Boulter D. 1987. A novel 4 mechanism of insect resistance engineered into tobacco. *Nature* 330:160-163). Regev et al. found that chitinase could dramatically increase the insecticidal activities of the insecticidal crystal proteins of Bt by degrading chitin layers of peritrophic membranes of insects (Regev A, Keller M, Strizhov N. 1996. Synergistic activity of a *Bacillus thuringiensis* delta-endotoxin and a bacterial endochitinase against *Spodoptera* littoralis larvae. *Appl Environ Microbiol* 62:3581-3586). After that, more and more synergistic effect-enhancing factors were discovered, such as zwiitermicin A, chaperone P20, bacteriolysin Cyt, cadherin fragment CR12—MPED etc. (Pardo-López L, Mũnoz-Garay C, Porta H, Rodrírguez-Almazán C, Soberón M, Bravo A. 2008. Strategies to improve the insecticidal activity of Cry toxins from *Bacillus thuringiensis*. *Peptides*. In press). These research results provide many very effective strategies to improve the insecticidal activities of *Bacillus thuringiensis* strains, or excellently postpone or overcome the resistance of insects thereon, thereby enormously promote the development of the industry of *Bacillus thuringiensis* insecticides and of the field of transgenic plants based on Bt.

SUMMARY OF THE INVENTION

The present invention isolates and clones a new enhancin gene bel1 from *Bacillus thuringiensis* YBT-1520, proves that the enhancin Bel1 has the function of improving the insecticidal activities of the insecticidal crystal proteins, and reveals the applications of the protein in the aspect of the control of agricultural pests.

The present invention is achieved as follows:

The applicant isolated a new enhancin gene bel1 from the YBT-1520 strain of *Bacillus thuringiensis* subsp. *kurstaki* (serotype, H3ab). By sequencing, it was found that the coding region of the enhancin gene bel1 of the present invention consisted of 2202 bases, having the nucleotide sequence as shown by SEQ ID NO: 1 of the sequence listing. It was discovered by analyzing the sequence that the enhancin Bel1 encoded by the bel1 gene of the present invention consisted of 733 amino acid residues, having the amino acid sequence as shown by SEQ ID NO: 1 of the sequence listing, and a molecular weight of 85 KDa as predicted. The applicant, by prokaryotic overexpression and indoor bioassay, proved that the Bel1 protein expressed by the bel1 gene of the present invention in microorganisms could remarkably improve the insecticidal activity of the insecticidal crystal protein Cry1Ac in killing Lepidoptera insects. Finally, the applicant revealed by constructing the genetically engineered bacteria of *Bacillus thuringiensis* containing enhancin Bel1 that the protein is of great application value for controlling the agricultural pest cotton bollworm.

The gene sequence above as provided by the present invention is a new enhancin gene which can be used for transforming microorganisms and plants to enable them to express enhancin Bel1 and to enable the receptor organism to express the trait possessed by the protein of remarkably improving the insecticidal activities of the insecticidal crystal proteins, and which can also be used for overcoming or postponing the problem of the resistance of pests against genetically engineered insecticides and transgenic plants, thereby is valuable for the wide applications in the biological control of agricultural pests.

The more detailed technical solutions are described with reference to the examples.

BRIEF DESCRIPTION OF THE DRAWINGS

SEQ ID NO.: 1 of the sequence listing is the gene sequence of the present invention and SEQ ID NO.: 2 of the sequence listing is the deduced sequence encoded thereby.

M: Protein Molecular Weight Standard

1: the total bacterial protein of non-induced control BL21/pGEX-6p-1 strain;

2: the total bacterial protein of BL21/pGEX-6p-1 strain induced by 1.0 mmol/L of IPTG for 3 h;

3: the total bacterial protein of non-induced BL21/pEMB0184 strain;

4: the total bacterial protein of BL21/pEMB0184 strain induced by 1.0 mmol/L of IPTG for 3 h;

5: GST-bel1 protein purified from induced BL21/pEMB0184 cultures by affinity chromatography;

6: GST protein purified from induced BL21/pGEX-6p-1 cultures by affinity chromatography.

FIG. 6: the scheme of constructing the shuttle expression vector pBMB0186 containing the enhancin gene bel1;

M: Protein Molecular Weight Standard

1: the total bacterial protein of BMB171 strain cultures after a 36 h culture;

2: the total bacterial protein of BMB0187 strain cultures after a 36 h culture.

DETAILED DESCRIPTION OF THE INVENTION

The following are the examples of the embodiments of the invention. It should be pointed out that the examples of the invention can be used as illustration of the invention only, but can not be used as limitation. For the standard operation methods of DNA and the used agents, see *Molecular Cloning: A Laboratory Manual* (see J. Sambrook et al. 2002. *Molecular Cloning: A Laboratory Manual*, Third Edition. trans. by Jin Dongyan et al. Science Press. Beijing). The other various experimental operations involved in the invention are all the conventional technologies in the art. For the portions with no particular explanations in the present text, an ordinary person skilled in the art may carry out them with reference to various reference books, scientific literatures or relevant specifications, manuals, etc., available before the filing date of the invention.

Example 1

Cloning the Enhancin Gene Bel1 in *Bacillus thuringiensis* YBT-1520

This invention used *Bacillus thuringiensis* YBT-1520 as a source strain of the enhancin gene bel1. For the source of the strain, see reference: Sun M, Liu Z, Yu Z. 2000. Characterization of the insecticidal crystal protein genes of *Bacillus thuringiensis* YBT-1520. *Wei Sheng Wu Xue Bao* 40: 365-371. The strain serotype is H3ab, which can form the typical rhombohedron crystals. The main crystal protein component has a molecular weight of about 130 kilodaltons (kDa). The strain has high specific toxicity towards the bollworm and the diamondback moth and other Lepidoptera insects. Currently, the whole genome of the strain has been sequenced by the applicant's group.

1. Extraction of Total DNA of *Bacillus thuringiensis* YBT-1520

*Bacillus thuringiensis* YBT-1520 was inoculated in a 5 mL LB culture medium with the inoculation loop by aseptic operations, placed in a shaker at 30° C., 200 rpm, overnight. 50 µL of the culture was then aseptically transferred to a 5 mL fresh LB culture medium, cultured under the same conditions to the log phase. Then, bacteria were collected by centrifugation, 5000 rpm, 3 min, washed once with 1 mL STE; a 100 µL solution I and 10 µL lysozyme (50 mg/mL) were added thereto, reacted at 37° C. for over 30 min. 200 µL 2% SDS was add for water bath at 50° C.-60° C. for 30 min. 200 µL NaCl (5 mol/L) was added to form a mixture. 500 µL phenol/chloroform/isoamyl alcohol (by volume ratio: 25:24:1) was added, centrifuged, 12000 rpm for 5 min. The supernatant was extracted. Extraction was repeated 1-2 times. Upper DNA solution was transferred to the Eppendorf tube. Adding an equal volume of 95% ethanol, standing at room temperature for 5 min and centrifuging, 12000 rpm, 5 min. Precipitates were washed once with 200 µL 70% ethanol, then frozen, dried by suction and dissolved in 50 µL TE solution.

2. PCR Amplification to Obtain DNA Fragments of the Gene Bel1

According to the sequence information in the full genome of YBT-1520, a pair of specific primers were designed and used to amplify the target gene bel1 (primer sequences: upstream belP1: 5'-GCCGGATCCATGTATACAAT-GTTTTTCCTC-3', downstream belP2: 5'-GGCGAATTCT-TATTCATTATATAAGCTATC-3'). PCR amplification was carried out with the total DNA of *Bacillus thuringiensis* prepared beforehand as the template. The system and procedures of PCR reaction were as follows:

The 25 µL, reaction system included: 2.5 µL 10×PCR reaction buffer, 1 µL dNTP (each 2.5 mM), 0.5 µL specific upstream primer P1 (20 mM), 0.5 µL specific downstream primer P2 (20 mM), 0.2 µL, template (the total DNA of YBT-1520 above), 0.25 µL ExTaq enzyme, sterile deionized water added until PCR reaction parameters and procedures were: 94° C., 5 min, 1 cycle; 94° C., 1 min, 52° C., 1 min, 72° C., 2.5 mM, 30 cycles; 72° C., 10 min, 1 cycle.

3. Bel1 Gene Sequencing and Sequence Analysis

Figure 1:
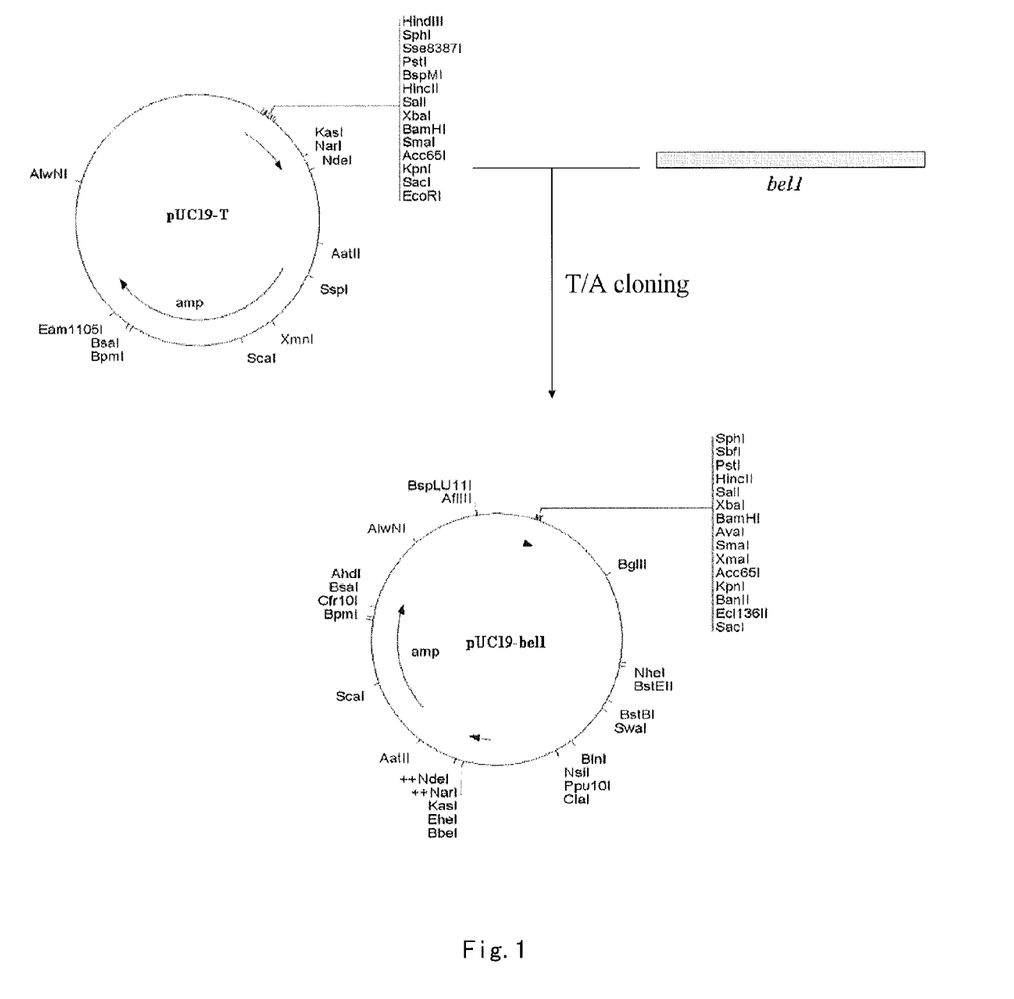
FIG. 1: the construction diagram of the cloning vector pUC19-bel1 constructed in the examples of the present invention.

PCR products were purified and recovered by a PCR product recovery kit (purchased from Omega Biotech Corporation) and then were linked to the T vector pMD19-Tsimple (purchased from TaKaRa Bio Inc.) by T/A cloning, to give the recombinant plasmid pUC19-bel1 containing the full-length gene of bel1 (see FIG. 1). Then, the recombinant plasmid was used for transforming *E. coli* DH5α, and was coated to an ampicillin resistant plate (Amp$^r$, the final concentration is 100 ug/ml). The resistant plate was cultured in an incubator at 37° C. for 12 h-16 h. When transformants grew to a certain size, with bel P1 and bel P2 as primers, the bacterial colonies of transformants as templates, the transformants were screened by PCR amplification. The screened positive transformants were cultured by being activated in 5 ml liquid, and then 1 ml sample of the overnight culture was taken and sent out for sequencing (Invitrogen). The sequencing result is the nucleotide sequence as listed in SEQ ID NO: 1, and the gene was named gene bel1. The software analyses predicted that this segment of coding sequence could encode a protein consisting of 733 amino acids, having a molecular weight of 85 kDa as predicted. It was named enhancin Bel1.

Example 2

Overexpression, Purification and Effect-Enhancing Activity of *Bacillus Thuringiensis* Enhancin Bel1

1. Constructing the Prokaryotic Overexpression Vector of *Bacillus thuringiensis* Enhancin Bel1

Figure 2:
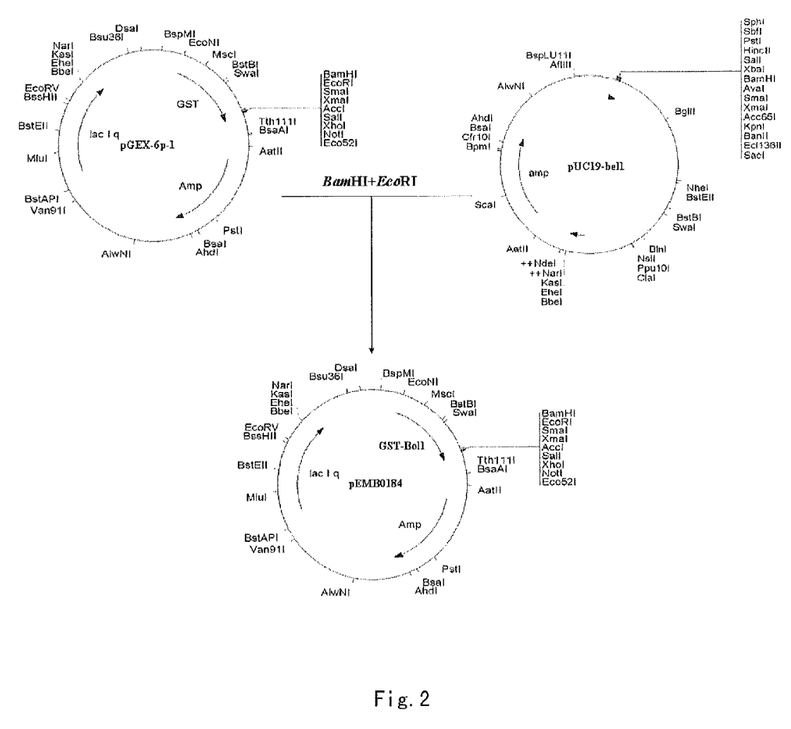
FIG. 2: the construction diagram of the overexpression vector pEMB0184 in the examples of the present invention.

The recombinant plasmid pUC19-bel1 containing the full-length bel1 gene obtained in Example 1 was subjected to double digestion by BamHI and EcoRI, while the plasmid pGEX-6p-1 was subjected to the same double digestion. After the aforesaid vector and exogenous digestion products were separated by 0.8% agarose gel, the target fragments were cut, purified and recovered by a DNA gel extraction kit (purchased from Omega Biotech Corporation). Then the two ones were linked by T4 ligase (purchased from TaKaRa Bio Inc.) to give a recombinant expression plasmid pEMB0184 containing the full-length ORF of bel1 (see FIG. 2). The recombinant expression plasmid was used to transform *E. coli* DH5α, and plasmids were extracted for respectively carrying out the double digestion of the BamHI and EcoRI for verification. The sizes of the digested fragments were consistent with the expected ones, and further sequencing results showed that the full-length ORF fragment of bel1 was correctly inserted into the expression vector pGEX-6p-1.

2. Prokaryotic Overexpression, Purification and Quantitative Analysis of *Bacillus thuringiensis* Enhancin Bel1

Figure 3:
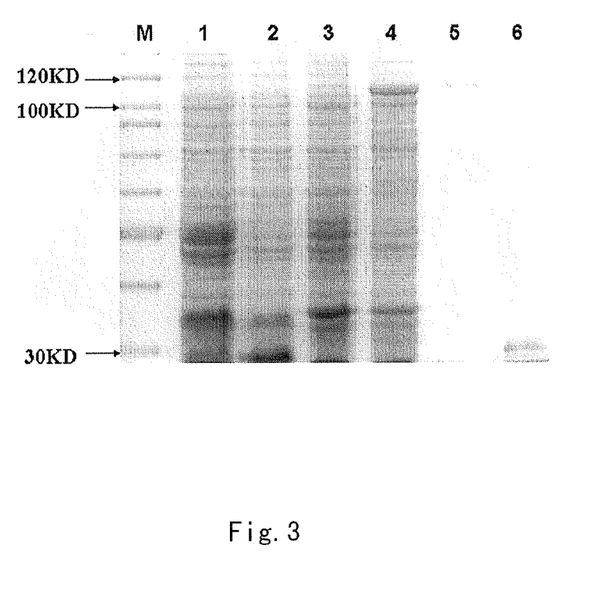
FIG. 3: SDS-PAGE electrophoretic analysis of the prokaryotic overexpression and purification of the enhancin gene bel1 cloned in the present invention.

For getting a great deal of enhancin Bel1, the aforesaid recombinant expression plasmid pEMB0184 carrying the full-length encoding gene of enhancin Bel1 was transformed into an *E. coli* overexpression dedicated receptor strain, BL21 (DE3), to give a recombinant strain BL21/pEMB0184. The recombinant strain was inoculated in 5 mL LB liquid medium (with ampicillin with a final concentration of 100 μg/mL), activated overnight. It was transferred at a ratio of 1:100 to 50 mL 2×YT liquid medium, cultured at 37° C. in a shaker until $OD_{600}$ was about 0.5-0.8, and then 1.0 mmol/L of IPTG was added, induced and cultured at 37° C. for 3 h. The resultant was centrifuged, 12000 rpm for 30 sec, and bacteria were collected, washed three times respectively with 0.5% NaCl and sterile deionized water. After that, the bacteria were mixed and homogenized again at a bacteria: sterile deionized water ratio of 1:5 by volume. An equal volume of 2× loading buffer was added and homogenized, treated in boiling water bath for 3-5 min, centrifuged, 12000 rpm for 5 min, and then the supernatant was subjected to SDS-PAGE electrophoresis. For the formulation of the 2× loading buffer and the operation steps of SDS-PAGE electrophoresis, see the method described by Laemmli (Laemmli, UK. 1970. Cleavage of structural proteins during the assembly of the head of bacteriophage T4. *Nature* (London) 227: 680-685). The results were shown in FIG. 3, compared with the empty vector BL21/pGEX-6P-1 as the control, BL21/pEMB0184 expressed a specific protein band, as shown in lane 4 of FIG. 3. In comparison with the protein molecular weight standard, it was estimated that the molecular weight of the specific protein was 113 kDa, coinciding with the expected molecular weight of the fusion enhancin GST-Bel1. It was proved that enhancin Bel1 was successfully expressed in *E. coli*.

The induced cultures above were centrifuged, 12000 rpm for 30 sec, and then bacteria were collected. Cells were broken by using ultrasound, then centrifuged, 12000 rpm for 15 min, and the supernatant was taken. Then the supernatant was purified by affinity chromatograph column (purchased from Novagen) to purify the specific protein GST-Bel1. For the concrete purification steps, see the operating instructions of the kit GST•Bind™ (Novagen). The final purified product was tested by SDS-PAGE electrophoresis. The results were shown in lane 5 of FIG. 3. The purified protein was consistent with the specific protein band expressed in BL21/pEMB0184 in terms of the size (as shown in lane 4 of FIG. 3), indicating that the purified specific protein was the fusion enhancin GST-Bel1. After that, the Bradford dyeing method (for the specific method, see Bradford M M. 1976. A rapid and sensitive method for the quantification of microgram quantities of protein utilizing the principle of protein-dye binding. *Anal Biochem* 72: 248-254.) was used to determine the content of the purified protein solution. The results showed that the purified enhancin solution had a concentration of 98.86 μg/ml.

3. Purification and Quantitative Analysis of Insecticidal Crystal Protein Cry1ac10

The *Bacillus thuringiensis* recombinant strain BMB171/cry1Ac10 carrying the crystal protein gene cry1Ac10 (deposited in our laboratory) was cultured in the ICPM medium for 48 h-52 h. The broth was dyed by fuchsin to produce a slide. When more than 90% of spores came off as observed by the optical microscope, the broth was centrifuged, 12000 rpm for 10 min at 4° C. The mixture of cells and crystals were collected, and then washed three times respectively with 1 mol/mL NaCl and distilled water, and then an appropriate amount of 50 mmol/mL $Na_2CO_3$ (3% β-mercaptoethanol, pH=9.5) was added, mixed thoroughly, in water bath at 37° C. for 60 min, centrifuged, 12000 rpm at 4° C. for 15 min, and precipitates were removed. The supernatant was added with one-twentieth the volume of 4 mol/mL NaAC-HAc (pH=4.0), stood on ice for 30 min, centrifuged while being frozen, 12000 rpm at 4° C. for 10 min. Precipitates were collected, washed with deionized water three times, and finally dissolved in 50 mmol/mL $Na_2CO_3$ (pH=9.5) to give the purified insecticidal crystal protein solution.

Likewise, the Bradford dyeing method was used for the determination of the content of the purified insecticidal crystal protein Cry1Ac10 solution, and the results showed that the purified Cry1Ac10 protein solution had a concentration of 748.1 μg/ml.

4 Determination of the Effect-Enhancing Activity of Enhancin Bel1 on the Insecticidal Action of the Insecticidal Crystal Protein Cry1Ac10

Newly incubated cotton bollworm (*Helicoverpa armigera*) larvae were used as the object to determine the effect-enhancing activity enhancin Bel1 on the insecticidal action of the insecticidal crystal protein Cry1Ac10. The specific bioassay procedures were in accordance with standard determination procedures (see: Shen Juqun, Wang Jinju, Yu Ziniu. 1990. Bioassay procedures and methods of Standardization of *Bacillus thuringiensis*. Chinese Journal of Biological Control, (Suppl.): 12-16). The bioassay of each sample was repeated three times, and the $LC_{50}$ was calculated.

Two tests were designed for detecting the effect-enhancing activity of the enhancin Bel1 on the insecticidal action of the insecticidal crystal protein Cry1Ac10.

Figure 4:
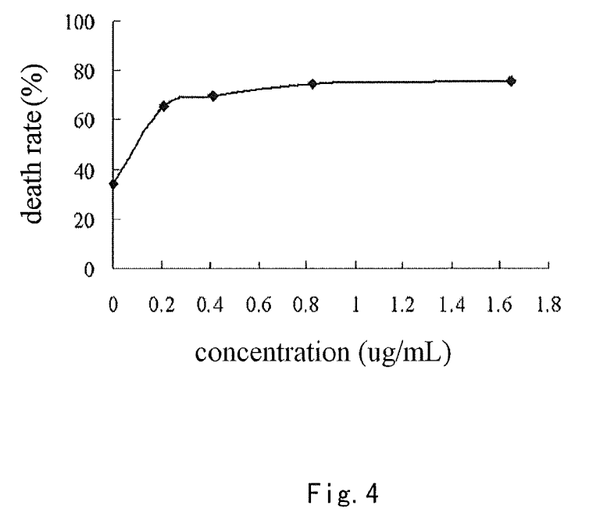
FIG. 4: Analysis 1 of the bioassay results of the enhancin Bel1 in the examples of the invention in different concentration ratios to the insecticidal crystal protein.

In the first test, firstly, the finally used concentration of the insecticidal crystal protein Cry1Ac10 in the feed was fixed as 3 μg/ml. The enhancin Bel1 solutions with different concentrations were mixed with the insecticidal crystal protein Cry1Ac10 and then added to the feed for bioassay. Five concentration ratios were set up: the ratios of the enhancin Bel1 to the insecticidal crystal protein Cry1Ac10 were 0:15, 1; 15; 2:15, 4:15, 8:15, respectively. The group using Cry1Ac10 alone, viz the group at the ratio of 0:15, was used as the control. The results were shown in FIG. 4. The 3 μg/ml Cry1Ac10 alone in the control group could induce a death rate of 34.2%, and when the 0.2 μg/ml enhancin Bel1 was added thereto, the death rate caused thereby rose sharply to 65.3%. When the concentration of the enhancin Bel1 continued to increase, the death rate rose to 76.2%. These results suggested that the enhancin had the remarkable effect of enhancing the insecticidal toxicity of the insecticidal crystal protein Cry1Ac10, and the effect of effect-enhancing increased with the rising of the enhancin Bel1 concentration.

Figure 5:
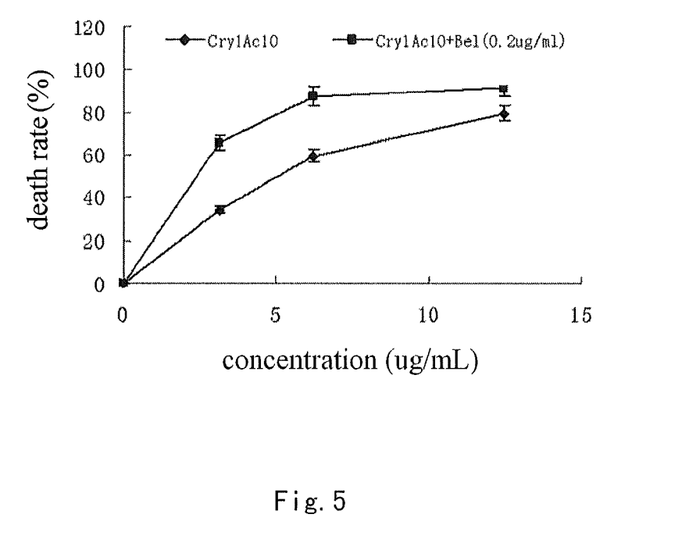
FIG. 5: Analysis 2 of the bioassay results of the enhancin Bel1 in the examples of the invention in different concentration ratios to the insecticidal crystal protein.

In the second experiment, the finally used concentration of the enhancin Bel1 in the feed was fixed as 0.2 μg/ml, the insecticidal crystal protein Cry1Ac10 solutions with different concentrations were mixed with the enhancin Bel1, and then added into the feed for the bioassay. Four concentration ratios were set up: the ratios of the enhancin Bel1 to the insecticidal crystal protein Cry1Ac10 were 1:0, 1; 15; 1:30, 1:60, respectively. The group using Cry1Ac10 alone was used as the control. The results were shown in FIG. 5. It was clear that at the four used concentration ratios, the death rates of the tested insects of the groups in which the enhancin Bel1 and Cry1AC10 are used in mixture were significantly higher than the death rates of the groups of Cry1AC 10 at different concentrations without the enhancin added. The results above further illustrated that the enhancin had the significant effect of enhancing the insecticidal toxicity of the insecticidal crystal protein Cry1Ac10.

Example 3

The Use of the Enhancin Bel1 for Constructing the Highly Effective Insecticidal Genetically Engineered Bacteria of *Bacillus Thuringiensis*

Example 2 proved that the enhancin Bel1 purified in vitro had the significant effect of enhancing the insecticidal toxicity of the insecticidal crystal protein Cry1Ac10. This portion utilized this characteristic of the protein for constructing a highly effective insecticidal genetically engineered bacterium strain of *Bacillus thuringiensis*. The specific steps were as follows:

1. constructing the shuttle expression vector of *E. coli-Bacillus thuringiensis* containing the enhancin Bel1

For enabling the enhancin gene bel1 to be expressed in *Bacillus thuringiensis*, the method of splicing by overlap extension (SOE) was used to add the promoter of the gene per se before the initiation codon of the coding region thereof. The construction scheme was shown in FIG. 6. Because the fragment was too long, the approach of segmental amplification was used to link the promoter and the coding region of the gene. Firstly, a pair of primers was designed according to the upstream promoter sequence of the gene bel1 on the genome of YBT-1520, p1: 5'-TGCGGATCCCGTTAAGTTTCTC-3', p2: 5'-AACAAGTAACCTTTTCATAAGTTACCTC-CATCTCTT-3'. Another pair of primers was designed according to the gene bel1 sequence on the plasmid pUC19-bel1, p3: 5'-CTGTGGTAAGTTATTATCGCCGTACGCGC-3'; p4: 5'-GGATCAACTAGAGCTCTTGC-3'. With the total DNA of YBT-1520 as the template, a fragment of about 900 bp of the promoter of the gene bel1 was amplified by using primers p1 and p2, the 3' end of which had the first 1-20 bases of the gene coding region of the gene bel1. With the DNA of the plasmid pUC19-bel1 as the template, the region bel1-1 of 1-1400 bases of the coding region fragment of the gene bel1 was amplified by using primers p3 and p4, the 5' end of which had the 20 bases of the end of the promoter fragment of bel1. After the two amplified products were purified, the two DNA fragments were mixed as templates, and the second round of PCR amplification was carried out by using primers p1 and p4 to give the fragment of about 2.2 kb, that is, gene pro-bel1-1. Finally, sequencing proved that the promoter pro3A was correctly linked with the gene coding region of the gene bel1.

The resultant pro-bel1-1 gene fragment was subjected to double digestion by BamHI and SacI and then inserted into the corresponding multiple cloning sites of the shuttle vector pHT304 of *E. coli-Bacillus thuringiensis* (for the vector source, see: Arantes O and Lereclus D. 1991. Construction of cloning vectors for *Bacillus thuringiensis*. Gene 108: 115-119) to yield the recombinant plasmid pBMB0185 having a size consistent with the expected fragment size as verified by digestion.

For obtaining a complete bel1 gene, with another pair of specific primers p5: 5'-GCAAGAGCTCTAGTTGATCC-3' and p6: 5'-CTGCCGAATTCTGAGAAGGT-3', and the DNA of pUC19-bel1 as the template, the rest fragment bel1-2 of about 800 bp of the gene bel1 was amplified. Then, it was digested by SacI and EcoRI, inserted into the corresponding multiple cloning sites of pBMB0185 to give the shuttle expression plasmid pBMB0186 containing the complete promoter and coding region of the gene bel1, having a size consistent with the expected fragment size as verified by digestion.

2. Constructing the Coexpression Vector of the Enhancin Bel1 and the Insecticidal Crystal Protein Cry1Ac10

Figure 7:
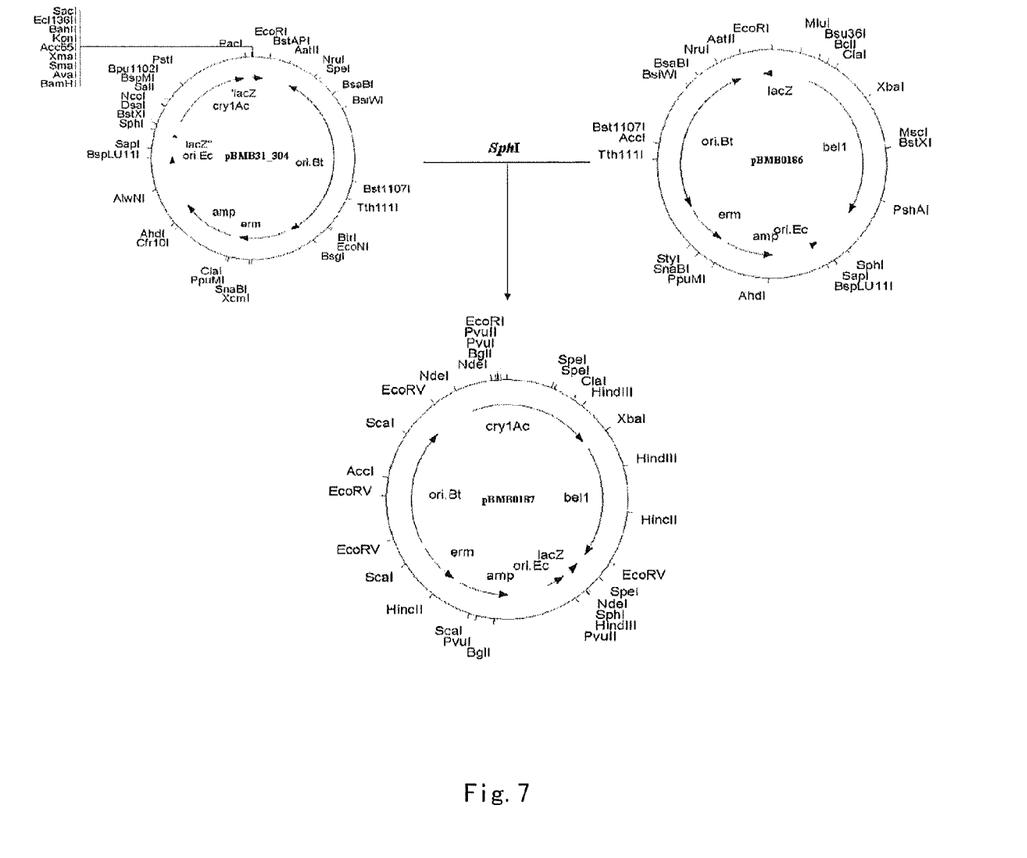
FIG. 7: the scheme of constructing the co-expression vector pBMB0187 of the enhancin Bel1 and the insecticidal crystal protein Cry1Ac10.

For taking advantage of the characteristic possessed by the enhancin Bel1 of enhancing the insecticidal toxicity of the insecticidal crystal protein Cry1Ac10, the enhancin Bel1 and the insecticidal crystal protein Cry1Ac10 were co-expressed in *Bacillus thuringiensis* BMB171. The construction of the coexpression vector was shown in FIG. 7, the complete promoter and coding region of the insecticidal crystal protein gene cry1Ac10 were cut down from the plasmid pBMB31__304 with a Sph1 single digestion, and inserted into the Sph1 site of the shuttle expression plasmid pBMB00186 containing the complete promoter and coding region of the gene bel1 to give the expression plasmid containing both the gene bel1 and the gene cry1Ac10. The digestion test proved that the digested product had a size consistent with the expected fragment size, indicating that the construction was correct. The recombinant plasmid was named pBMB0187.

3. The Expression of the Enhancin Gene Bel1 in *Bacillus thuringiensis* BMB171

For testing whether the enhancin gene bel1 could be normally expressed in BMB171, the electroporation method (Wu Lan, Sun Ming, Yu Ziniu, A new resolution vector with cry1Ac10 gene based on *Bacillus thuringiensis* transposon Tn4430, Acta Microbiol Sinica, 2000, 40: 264-269) was used to transform the constructed coexpression recombinant plasmid pBMB0187 above into *Bacillus thuringiensis* acrystalliferous mutant strain BMB171 (for the strain source, see: Li L, Yang C, Liu Z D, Li F L, Yu Z N. 2000. Screening of acrystalliferous mutants from *Bacillus thuringiensis* and their transformation properties. *Acta Microbiol Sinica* 5: 395-399). The resistance screening and the digestion proved that the correct transformant BMB0187 was obtained.

Figure 8:
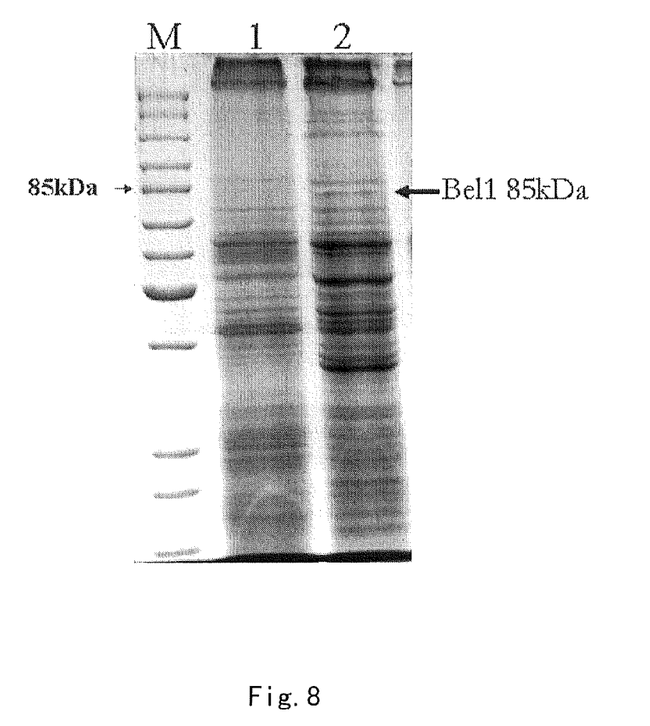
FIG. 8: the SDS-PAGE electrophoretic analysis of the expression of the enhancin gene bel1 in *Bacillus thuringiensis* BMB171.

The engineered bacterium above was activated overnight in LB medium (erythromycin with a final concentration of 20 μg/mL added during the use), then transferred to ICPM medium (erythromycin with a final concentration of 20 μg/mL added during the use), cultured until spores were fully mature and came off, and bacteria were collected. The bacteria were washed three times respectively with 0.5% NaCl and sterile deionized water, then mixed again uniformly in accordance with a ratio of bacteria: sterile deionized water=1:5 by volume. An equal volume of 2× loading buffer was added, homogenized, processed in boiling water bath for 3-5 min, centrifuged, 12000 rpm for 5 min. The supernatant was subjected to SDS-PAGE electrophoresis. As shown in FIG. 8, BMB0187 could express the specific protein having the same size as expected. Compared with the molecular weight standard, it was estimated that the molecular weight thereof was 85 kDa, while the BMB171 as the negative control (containing only the shuttle vector pHT304) did not have the corresponding band. This indicated that the enhancin gene bel1 was expressed in *Bacillus thuringiensis* BMB171. It was further proved by the observation through the electron microscopy that the recombinant bacterium could well form typical rhombohedron crystals, indicating that the expression of the enhancin gene bel1 in *Bacillus thuringiensis* BMB171 did not affect the normal expression of the insecticidal crystal protein Cry1Ac10. The results above demonstrated that the genetically engineered bacterium co-expressing the enhancin Bel1 and the insecticidal crystal protein Cry1Ac10 was successfully obtained. It was named bel1-transgenic *Bacillus thuringiensis* genetically engineered bacterium BMB0187.

4. The Indoor Bioassay of *Bacillus thuringiensis* Highly Effective Insecticidal Engineered Bacterium BMB0187 Against Cotton Bollworms For testing the insecticidal activity of the engineered bacterium BMB0187, the newly incubated cotton bollworm (*H. armigera*) larvae were used as the object to determine the insecticidal effects of the engineered strain and the initial strain thereof. The engineered bacterium BMB0187 and the recombinant bacterium BMB171/cry1Ac10 containing only Cry1Ac10 were activated overnight in LB medium (erythromycin with a final concentration of 20 μg/mL added during the use), and then transferred to 30 ml ICPM medium according to the 1:100 inoculum (erythromycin with a final concentration of 20 μg/mL added during the use), cultured until spores were about to mature and come off. The resultant bacteria were collected and washed once with sterile deionized water to give a parasporal crystal mixture, which was subjected to bioassay in accordance with the standard test procedures (see: Shen Juqun, Wang Jinju, Yu Ziniu. Bioassay procedures and methods of Standardization of *Bacillus thuringiensis*. Chinese Journal of Biological Control, 1990, (Suppl.): 12-16). The bioassay of each sample was repeated three times, and the $LC_{50}$ was calculated by the professional statistical software DPS. The results were shown in Table 1. According to the death rates of the corresponding concentrations and the calculated $LC_{50}$ in the table, it can be seen that the engineered bacterium BMB0187 introduced with the bel1 gene had an insecticidal toxicity against cotton bollworms significantly higher than that of the BMB171/cry1Ac10 strain to which the bel1 gene was not introduced, and the relative effect-enhancing fold reached 5.7 times.

TABLE 1

The insecticidal activities towards cotton bollworms of EMB171/cry1Ac10 strains and strains of engineered bacterium BMB0187

| Strain | Genotype | $LC_{50}$ (μL/mL) | Effect-Enhancing Fold |
|---|---|---|---|
| BMB171/cry1Ac10 | cry1Ac10 | 0.51 | 1 |
| BMB0187 | cry1Ac10 + bel1 | 0.09 | 5.7 |

The results above indicate that the engineered bacterium BMB0187 has an insecticidal activity increased by almost five times as compared with that of the initial strain BMB171/cry1Ac10 containing only Cry1Ac10. Then, when the product is used for cotton bollworm controlling, while achieving the same insecticidal effect, the used amounts of Bt agricultural chemical can be dramatically reduced so that a great amount of production costs are saved. In addition, Bel1 protein itself comes from *Bacillus thuringiensis*, so the transgenic security problem does not exist. Thus, the engineered bacterium is of good application value.

The invention claimed is:

1. An isolated enhancing bel1 gene from *Bacillus thuringiensis*, wherein said gene comprises the nucleotide sequence of SEQ ID NO: 1.

2. An isolated bel1 protein from *Bacillus thuringiensis* comprising the amino acid sequence of SEQ ID NO: 2, wherein said bel1 protein is encoded by the isolated gene according to claim 1.

3. A recombinant DNA construct comprising the isolated bel1 gene according to claim 1.

4. A micro-organism for controlling agricultural pests comprising the recombinant DNA construct according to claim 3.

5. A plant cell for controlling agricultural pests transformed with the nucleic acid sequence according to claim 1.

* * * * *

SEQUENCE LISTING

```
<160> NUMBER OF SEQ ID NOS: 2

<210> SEQ ID NO 1
<211> LENGTH: 2202
<212> TYPE: DNA
<213> ORGANISM: Bacillus thuringiensis

<400> SEQUENCE: 1
atgtatacaa tgtttttcct cataggaaat atacacttac atgctgatga acgaataaat      60
gcaaaaaaaa ttactagttt agaagagcct acttggatat ttcaggcggg cataagtaag     120
gggaaatatc atgaccgaca agatttagga tttattttga agagaaatac accattaaag     180
gtaagacaaa caaatcctaa tttaaagac aaattaacat tacgtttatt gtctaatgac      240
tcaaaaaatg aaaaatccat acaagtagga aatgaatggg ttactatcca aggtgatacg     300
tctttagttc ctttcataga tactccgtat ggtgaagagc acgctgtact tgagtaccaa     360
gtagggaatg aaagtgctac taacccccctt cccatttata aacaacaagg aagtgtatct    420
```

```
caatttttta gtacatggga tcaatttgat ggagagtatg cgttacttca aggggagagt    480
tttcaattat ttgtacctaa aaaagataaa gagttagtaa gatctttaaa agattttcaa    540
tcattggatg agttaattgc gtattatgaa gatattttg tgatgtatga ttcaattatt    600
ggtttagatg gctcaacgtt tgaaaataaa aaaagtcaaa atcgttattt cttaaaagca    660
gatatatctg gtgctggcgg tgcctattat ggcacaaatt ggacagcgaa tagtacagat    720
agtacaaaga tgtggttaga taaactaagt tggggaactt acatgaaat cgctcatgga    780 taccaagctg gttttgataa tcaaggaata tttacaggag aagtttctaa taatctatt    840 ggtgttcaat atcaatatag taaatacggc aaaaaagcag atcaagttgg ttggttgttt    900
aatttcggga aaaaggaaca ggtagaacgg aatttatata atgctttaat gaaagaaaat    960
aaaaattatg atgatttaga tttacgacaa aaacttattc ttttaacgat ggcgaaacaa   1020
aaagctggcg atgaagcatt tgcaaaaatg tatcaaggtt atcgaaaact agctagcaat   1080
gctgctttca aaaaggtga ccattctta ccagatttaa tgaatcagta ttatagtgag   1140
aatggacaag ttgattttac acctgttttt gaaagatggg gctttaagct taatcataaa   1200
caaatagaga tgaatagggc gaaaggtttt ccggctgtta cttcttagc ttatatagtg   1260 cctgaatcac aattagcgaa agcaagagct atagttgatc ctgatattcc gataaactcc   1320
aacttcgaaa tagttacgaa tcagcaaatt gctccacttg ggctaaaagg gaatttgcat   1380
atccatttaa atacaaatga aatagataca ttaaaaggag gaaaaattaa attaaaagaa   1440
gggaatacag ttattcaaga gaaacaattg gaaacaacag atatcaattt acaagacgta   1500
ccaaatggag tgtatacggt tgaaatttca ggtgggaaaa cgaatagtat gtaccatttc   1560
agttcgtatt atgcctatgt aaaagaaaaa gataatagtc taaagattga tattaacgaa   1620
atgaaagtga gtaagttggt aaatgaaacg attcaattcc taggattagg agatgaccag   1680
tttgccgtat aaatacaga cttagagcaa atcgagcta ttttacgat tactactaaa   1740 acgcctcata gctattatgc aggtgaaaaa tatgcatcga tagaggtctt taatgaaaaa   1800
ggtgaaaaaa tttatacgaa ggaaatggaa ggaacaaatg taacaattgt aaaagatatc   1860
attccactaa aagagggata tagaattaaa atctatcatg atgaaataaa aaacgatta   1920 actagtaaag ctactattat taatcctatg aataaaatga atgaatttat aataacaaaa   1980
tggggattga aaaatacttc tttgcaaaat aatccagaag aaaatcttat acaagaatt   2040 gatgaagaaa tggaagcgat tataggtaat cagtttttaa agagataccc aatgcaaaaa   2100
ttagaaatga aaagaatgt gtggatggca ataaatatgt tatcagaacc acaaaaaata   2160
acgtatatga ataaatataa agatagctta tataatgaat aa                      2202
```

<210> SEQ ID NO 2
<211> LENGTH: 733
<212> TYPE: PRT
<213> ORGANISM: Bacillus thuringiensis

<400> SEQUENCE: 2

Met Tyr Thr Met Phe Phe Leu Ile Gly Asn Ile His Leu His Ala Asp
1               5                   10                  15

Glu Arg Ile Asn Ala Lys Lys Ile Thr Ser Leu Glu Glu Pro Thr Trp
            20                  25                  30

Ile Phe Gln Ala Gly Ile Ser Lys Gly Lys Tyr His Asp Arg Gln Asp
        35                  40                  45

Leu Gly Phe Ile Leu Lys Arg Asn Thr Pro Leu Lys Val Arg Gln Thr
    50                  55                  60

```
Asn Pro Asn Phe Lys Asp Lys Leu Thr Leu Arg Leu Leu Ser Asn Asp
 65                  70                  75                  80

Ser Lys Asn Glu Lys Ser Ile Gln Val Gly Asn Glu Trp Val Thr Ile
                 85                  90                  95

Gln Gly Asp Thr Ser Leu Val Pro Phe Ile Asp Thr Pro Tyr Gly Glu
            100                 105                 110

Glu His Ala Val Leu Glu Tyr Gln Val Gly Asn Glu Ser Ala Thr Asn
        115                 120                 125

Pro Leu Pro Ile Tyr Lys Gln Gln Gly Ser Val Ser Gln Phe Phe Ser
130                 135                 140

Thr Trp Asp Gln Phe Asp Gly Asp Tyr Ala Leu Leu Gly Glu Ser
145                 150                 155                 160

Phe Gln Leu Phe Val Pro Lys Lys Asp Lys Glu Leu Val Arg Ser Leu
                165                 170                 175

Lys Asp Phe Gln Ser Leu Asp Glu Leu Ile Ala Tyr Tyr Glu Asp Ile
            180                 185                 190

Phe Val Met Tyr Asp Ser Ile Ile Gly Leu Asp Gly Ser Thr Phe Glu
        195                 200                 205

Asn Lys Lys Ser Gln Asn Arg Tyr Phe Leu Lys Ala Asp Ile Ser Gly
210                 215                 220

Ala Gly Gly Ala Tyr Tyr Gly Thr Asn Trp Thr Ala Asn Ser Thr Asp
225                 230                 235                 240

Ser Thr Lys Met Trp Leu Asp Lys Leu Ser Trp Gly Thr Leu His Glu
                245                 250                 255

Ile Ala His Gly Tyr Gln Ala Gly Phe Asp Asn Gln Gly Ile Phe Thr
            260                 265                 270

Gly Glu Val Ser Asn Asn Leu Phe Gly Val Gln Tyr Gln Tyr Ser Lys
        275                 280                 285

Tyr Gly Lys Lys Ala Asp Gln Val Gly Trp Leu Phe Asn Phe Gly Lys
290                 295                 300

Lys Glu Gln Val Glu Arg Asn Leu Tyr Asn Ala Leu Met Lys Glu Asn
305                 310                 315                 320

Lys Asn Tyr Asp Asp Leu Asp Leu Arg Gln Lys Leu Ile Leu Leu Thr
                325                 330                 335

Met Ala Lys Gln Lys Ala Gly Asp Glu Ala Phe Ala Lys Met Tyr Gln
            340                 345                 350

Gly Tyr Arg Lys Leu Ala Ser Asn Ala Ala Phe Lys Lys Gly Asp His
        355                 360                 365

Ser Leu Pro Asp Leu Met Asn Gln Tyr Tyr Ser Glu Asn Gly Gln Val
370                 375                 380

Asp Phe Thr Pro Val Phe Glu Arg Trp Gly Phe Lys Leu Asn His Lys
385                 390                 395                 400

Gln Ile Glu Met Asn Arg Ala Lys Gly Phe Pro Ala Val Thr Ser Leu
                405                 410                 415

Ala Tyr Ile Val Pro Glu Ser Gln Leu Ala Lys Ala Arg Ala Ile Val
            420                 425                 430

Asp Pro Asp Ile Pro Ile Asn Ser Asn Phe Glu Ile Val Thr Asn Gln
435                 440                 445

Gln Ile Ala Pro Leu Gly Leu Lys Gly Asn Leu His Ile His Leu Asn
        450                 455                 460

Thr Asn Glu Ile Asp Thr Leu Lys Gly Lys Ile Lys Leu Lys Glu
465                 470                 475                 480

Gly Asn Thr Val Ile Gln Glu Lys Thr Ile Glu Thr Thr Asp Ile Asn
                485                 490                 495
```

-continued

```
Leu Gln Asp Val Pro Asn Gly Val Tyr Thr Val Glu Ile Ser Gly Gly
            500                 505                 510

Lys Thr Asn Ser Met Tyr His Phe Ser Ser Tyr Tyr Ala Tyr Val Lys
        515                 520                 525

Glu Lys Asp Asn Ser Leu Lys Ile Asp Ile Asn Glu Met Lys Val Ser
    530                 535                 540

Lys Leu Val Asn Glu Thr Ile Gln Phe Leu Gly Leu Gly Asp Asp Gln
545                 550                 555                 560

Phe Ala Val Leu Asn Thr Asp Leu Glu Gln Asn Arg Ala Ile Phe Thr
                565                 570                 575

Ile Thr Thr Lys Thr Pro His Ser Tyr Tyr Ala Gly Glu Lys Tyr Ala
            580                 585                 590

Ser Ile Glu Val Phe Asn Glu Lys Gly Glu Lys Ile Tyr Thr Lys Glu
        595                 600                 605

Met Glu Gly Thr Asn Val Thr Ile Val Lys Asp Ile Ile Pro Leu Lys
    610                 615                 620

Glu Gly Tyr Arg Ile Lys Ile Tyr His Asp Glu Ile Lys Lys Arg Leu
625                 630                 635                 640

Thr Ser Lys Ala Thr Ile Ile Asn Pro Met Asn Lys Met Asn Glu Phe
                645                 650                 655

Ile Ile Thr Lys Trp Gly Leu Lys Asn Thr Ser Leu Gln Asn Asn Pro
            660                 665                 670

Glu Glu Asn Leu Ile Gln Arg Ile Asp Glu Glu Met Glu Ala Ile Ile
        675                 680                 685

Gly Asn Gln Phe Leu Lys Glu Ile Pro Met Gln Lys Leu Glu Met Lys
    690                 695                 700

Lys Asn Val Trp Met Ala Ile Asn Met Leu Ser Glu Pro Gln Lys Ile
705                 710                 715                 720

Thr Tyr Met Asn Lys Tyr Lys Asp Ser Leu Tyr Asn Glu
                725                 730
```